US006387955B1

(12) United States Patent
Biegon et al.

(10) Patent No.: US 6,387,955 B1
(45) Date of Patent: May 14, 2002

(54) ENHANCED ANTI-ANGIOGENIC ACTIVITY OF PERMANENTLY CHARGED DERIVATIVES OF STEROID HORMONES

(75) Inventors: Anat Biegon, Tel Aviv (IL); Marcus E. Brewster, Gainesville, FL (US)

(73) Assignee: Pharmos Corporation, Rehovot (IL)

( * ) Notice: Subject to any disclaimer, the term of this patent is extended or adjusted under 35 U.S.C. 154(b) by 0 days.

(21) Appl. No.: 09/562,949

(22) Filed: May 3, 2000

Related U.S. Application Data

(62) Division of application No. 08/833,074, filed on Apr. 2, 1997, now Pat. No. 6,083,990.

(51) Int. Cl.$^7$ ............................................... A61K 31/14

(52) U.S. Cl. ...................... 514/643; 514/114; 514/642; 514/717; 514/718

(58) Field of Search ................................ 514/114, 642, 514/643, 717, 718

(56) References Cited

U.S. PATENT DOCUMENTS

| | | | |
|---|---|---|---|
| 2,914,561 A | 11/1959 | Allen et al. | 564/324 |
| 2,914,562 A | 11/1959 | Allen et al. | 564/324 |
| 2,914,564 A | 11/1959 | Allen et al. | 564/324 |
| 2,971,001 A | 2/1961 | Palopolie et al. | 546/240 |
| 4,536,516 A | 8/1985 | Harper | 514/514 |
| 4,696,949 A | 9/1987 | Toivola et al. | 564/299 X |
| 4,973,755 A | 11/1990 | Grafe | 564/324 |

FOREIGN PATENT DOCUMENTS

| | | |
|---|---|---|
| EP | 0168175 | 6/1985 |
| WO | WO92/06068 | 4/1992 |

OTHER PUBLICATIONS

Dorland's Illustrated Medical Dictionary, 1995, pp. 740–1, 801, 1450, 1455, 1495 and 1576.
Jarman et al., "Analogues of tamoxifen: the role of the basic side chain. Applications of a whole–cell oestrogen–receptor binding assay to N–oxides and quaternary salts", Cancer Drug Design, 1, 159–268, 1986.
Jordan, "A current view of tamoxifen for the treatment and prevention of breast cancer", Br. J. Pharmacol. 110, pp. 507–517, 1993.
Vr. J. Pharmacol. (1993), 110, 507–517, "A current view of tamoxifen for the treatment and prevention of breast cancer", by V. Craig Jordan.
Cancer Drug Design (1986), 1, 259–268, "Analogues of tamoxifen: the role of the basic side–chain. Applications of a whole–cell oestrogen–receptor binding assay to N–oxides and quaternary salts", by M. Jarman, et al.
Pharmacology 1992; 45, 329–337, "Effects of Nonsteroidal Antiestrogens in the in vitro Rat Uterus", by Begona Cantabrana et al.

Neuroscience Research 4, 65–99 (1971), "Site of Action and Active Form of Local Anesthetics", Toshio Narashashi, et al.
Annals New York Academy of Sciences, "Novel Pure Anti–estrogens, Mode of Action and Therapeutic Prospects", by A.E. Wakeling (1991).
Endocrine Therapies of Cancer, "Cancer Chemotherapy", by Bruce A. Chabner et al. (1990).
Reports 1477, vol. 83, No. 20, Oct. 16, 1991, "Acquired Tamoxifen Resistance: Correlation with Reduced Breast Tumor Levels of Tamoxifen and Isomerization of Trans–4–Hydroytamoxifen", by C. Kent Osborne et al.
Endocrinology, vol. 123, No. 4, 1747–1753, "Differential Induction of Progestin–Binding Sites in Uterine Cell Types by Estrogen and Antiestrogen", by Bruce E. Ennis et al. (1988).
Eur J Cancer, vol. 29A, No. 4, 589–592, 1993, "Breast Cancer Chemoprevention", by Alberto Costa.
Annals of Medicine 25, 105–111, 1993, "Development of a Preclinical Model for Hormonal Therapy of Human Endometrial Carcinomas", by P.G. Satyaswaroop.

(List continued on next page.)

Primary Examiner—Dwayne C. Jones
(74) Attorney, Agent, or Firm—Winston & Strawn

(57) ABSTRACT

The present invention discloses the use of permanently charged steroid agonists or antagonists as potent anti-angiogenic compositions comprising as an active ingredient a compound of the general formulae I, II or III:

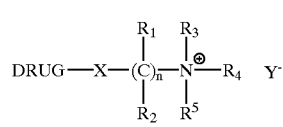

I

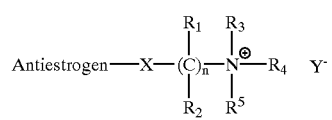

II

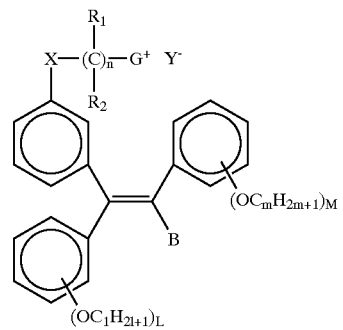

III wherein DRUG is any steroid agonist or antagonist, a mixed agonist-antagonist, or a partial agonist and the substituents are as defined in the specification.

19 Claims, 6 Drawing Sheets

OTHER PUBLICATIONS

Academic Press Limited, Cancer Treatment Reviews (1993), 19 (Supplement B), 11–19, "Impact of adjuvant chemotherapy in breast cancer on response to tamoxifen at relapse", by Phillippa G. de Takats, et al.

Endocrinology, 1986, vol. 119, No. 6, 2261–2669, "Antiestrogen Action in the Medial Basal Hypothalamus and Pituitary of Immature Female Rats: Insights Concerning Relationships among Estrogen, Dopamine, and Prolactin", by Thomas W. Toney et al.

Journal of Endocrinology, 1991, 130, 409–414, "Pharmacological characterization of a novel oestrogen antagonist, ZK 119010, in rats and mice", by Y. Nishino et al.

Endocrinology, 1991, vol. 129, vol. 129, No. 3, 1568–1574, "Dose Dependent Effects of Tamoxifen on Long Bones in Growing Rats: Influence of Ovarian Status", by Lilly Y. Moon.

—□— TMI    —◇— Tam

—□— TMI    —◇— Tam

◩ Tamoxifen    ▨ TMI

Concentration (uM)

| Vehicle | TMI-(MMP-9) |
| TMI-(MMP-2) | TBzBr-(MMP-9) |
| TBzBr-(MMP-2) | |

ENHANCED ANTI-ANGIOGENIC ACTIVITY OF PERMANENTLY CHARGED DERIVATIVES OF STEROID HORMONES

CROSS-REFERENCE TO RELATED APPLICATION

This application is a division of U.S. application Ser. No. 08/833,074 filed Apr. 2, 1997, now U.S. Pat. No. 6,083,990.

FIELD OF THE INVENTION

This invention relates to pharmaceutical compositions that are useful for the treatment or prevention of pathological angiogenesis or conditions requiring prevention of angiogenesis. More particularly, this invention relates to the use of quaternary derivatives of steroid agonists or antagonists having improved anti-angiogenic properties.

BACKGROUND OF THE INVENTION

Angiogenesis

Angiogenesis is a complex process in which capillary blood vessels grow in an ordered sequence of events (Folkman and Klagsbrun, Science 235, 442–447, 1987; Folkman and Shing, J. Biol. Chem. 267, 10931–10934, 1992). A substantial body of evidence supports the hypothesis that tumor angiogenesis is fundamental for the growth and metastasis of solid tumors (Folkman and Klagsbrun ibid., 1987; Weidner et al. Amer. J. Pathol. 143, 401–409, 1993; O'Reilly et al. Cell 79, 316–328, 1994). Indeed, the majority of clinical tumors are not even clinically detectable until after the occurrence of neovascularization, whose induction in solid tumors is mediated by one or more angiogenic factors.

Furthermore, angiogenesis is also important in a number of other pathological processes, including, but not limited to, arthritis, psoriasis, diabetic retinopathy, retinopathy of prematurity, macular degeneration, scleroderma, hemangioma, retrolental fibroplasia, abnormal capillary proliferation in hemophiliac joints, prolonged menstruation and other disorders of the female reproductive system. Thus, methods of blocking angiogenesis are clearly necessary.

The basic mechanism of angiogenesis may be outlined briefly as follows. When a new capillary sprouts from the side of a venule, endothelial cells degrade the basement membrane, migrate toward an angiogenic source, proliferate, form a lumen, join the tips of two sprouts to generate a capillary loop, and manufacture a new basement membrane (Folkman, Perspectives in Biology and Medicine, 29, 1–36, 1985).

Degradation and remodeling of the extracellular matrix (ECM) are essential processes for the mechanism of angiogenesis. In addition, ECM components synthesized by endothelial cells (i.e., collagens, laminin, thrombospondin, fibronectin and SPARC) function to regulate endothelial cell growth, migration and shape (Bischoff, Trends Cell Biol. 5, 69–744, 1995). Bovine aortic endothelial cells (BAE), while undergoing sprouting and tube formation, synthesize collagen and SPARC. It has been proposed that type I collagen may be involved in directing the migration and assembly of BAE cells (Iruela-Arispe et al. Lab. Invest. 64, 174–186, 1991).

In order to treat angiogenesis related disorders, several inhibitors of the angiogenesis mechanism are being studied, including platelet factor 4, the fumagillin derivative AGH 1470, Interferon ($\alpha_2$a, thrombospondin, angiostatic steroids, and angiostatin (Folkman ibid., 1995; O'Reilly et al., ibid., 1994). In addition, anti-estrogens have also been shown to inhibit angiogenesis (Garliardi and Collins, Cancer Res. 53, 533–535, 1993). Unfortunately, many of these inhibitors all share the property of being relatively non-specific in their effects and, therefore, potentially toxic. A more specific inhibitor would be most useful, particularly an inhibitor that would selectively block an underlying mechanism of angiogenesis without adversely affecting other physiological functions. Furthermore, many of the compounds that are now being evaluated as anti-angiogenic agents are proteins (e.g., antibodies, thrombospondin, angiostatin and platelet factor IV) which generally suffer from poor bioavailability and are readily degraded in the body. Hence, they must be administered in high doses and frequencies.

There is, thus, a widely recognized unmet need for an inhibitor of angiogenesis which specifically blocks the proliferation of vascular structures without substantially affecting other physiological processes—including an inhibitor of angiogenesis associated with tumor growth or progression.

Permanently Charged Steroid Hormones and Their Antagonists

Pharmaceutical therapies for breast cancer currently consists of hormonal and cytotoxic agents. Hormonal therapy was developed because, in many women, breast cancer cells have receptors for the steroid hormone estrogen. The growth of these estrogen receptor-positive cancer cells can be stimulated by estrogen. Anti-estrogen therapy attempts to reduce or stop the synthesis of estrogen or to block the action of estrogen on the cancer cell.

Among all hormonals, tamoxifen (U.S. Pat. No. 4,536,516) holds a prevalent position. Originally used as an anti-estrogen to treat breast cancer in patients with estrogen receptor-positive tumors, the drug was also found to slow the growth of breast cancer in women with estrogen receptor-negative tumors. Tamoxifen is, therefore, useful in most patients. The anti-estrogen tamoxifen is particularly effective in delaying recurrence in breast cancer patients and in the palliative treatment of advanced metastatic breast cancer. It is also useful in the treatment of gliomas and hepatomas as well as endometrial, uterine, ovarian and prostatic neoplasms (Litherland, S. et al. Cancer Treatment Reviews, 15, 183, 1988; Jordan, C., Br. J. Pharmacol., 110, 507, 1993).

Anti-estrogens, including tamoxifen, compete with estrogen for receptor sites in cancerous tissues. occupancy of the receptor site by an anti-estrogen fails to elicit the full spectrum of transcriptional actions generated by estrogens and, thus, blocks their activity. It is generally believed that estrogens function by first binding to the target cell cytosolic receptors, and then moving into the cell nucleus, where they affect DNA transcription.

Considerable effort has been invested in the development of novel tamoxifen analogs presumed to have improved therapeutic potential, by virtue of their increased selectivity as anti-estrogenic compounds (e.g., U.S. Pat. No. 4,973,755; EP 0 168,175) or their higher affinity for the estrogen receptor (WO 92/06068).

Hydrophilic compounds and particularly compounds with ionic charges (cationic or anionic) are often very poorly distributed into the CNS and brain since a lipophilic barrier (the blood-brain barrier) exists. One method for creating a permanent charge on a drug is the incorporation of a quaternary ammonium salt (nitrogen with four hydrocarbon groups attached). Tamoxifen and other anti-estrogens that contain an amino group can be quaternized (converted to a quaternary ammonium group). Such quaternization results in imparting a permanent positive charge to the parent molecule which should effectively reduce the molecule's penetration across physiological membranes which are inherently lipophilic and resistant to penetration of ions, particularly large ions.

Several quaternary salts of tamoxifen have been prepared and described in scientific publications (Jarman et al., Anti-cancer Drug Design, 1, 259, 1986). When tested in vitro, these derivatives were reported not to halt the proliferation of breast tumor cell lines grown in culture. These compounds were, therefore, predicted to be of no therapeutic value in vivo.

WO 95/26720 disclosed that unexpectedly ionic derivatives of the anti-estrogen tamoxifen, which were predicted to be of no value in vivo on the basis of their lack of activity in vitro, are, in fact, more active as anticancer agents in vivo than the parent compound. This invention is applicable, in principle, to a wide variety of other anti-estrogens where adverse side-effects may be reduced or eliminated by preventing access of the drugs to the CNS.

In a study of MCF-7 human breast cancer implanted in nude mice, TMI proved to be significantly more potent than tamoxifen in its anticancer action. TMI induced tumor regression that began almost immediately upon dose initiation and which resulted in complete regression of the implanted cancer in 40% of animals tested. The parent compound, tamoxifen, merely slowed tumor growth in that study (Cancer Res. 56, 4238, 1996).

While tamoxifen and other anti-estrogens have been reported to have angiostatic activity in tumors, the mechanism of inhibition of angiogenesis is not clear (Cancer Res. 54, 5511, 1994; Cancer Res. 53, 533, 1993).

SUMMARY AND OBJECTS OF THE INVENTION

According to the present invention, it is now disclosed that permanently charged steroid agonists and antagonists are unexpectedly potent anti-angiogenic agents. It is further disclosed that permanently charged anti-estrogens may mediate their anti-angiogenic effects by inhibiting the transcription of metalloproteases, including collagenases that are required for the restructuring of the extracellular matrix.

It is also the object of this invention to provide permanently charged steroid agonists and antagonists for the clinical treatment of protracted angiogenesis and other diseases and pathological conditions involving angiogenesis. The methods of the invention will be useful with a wide variety of steroid agonists and antagonists including, but not limited to, charged derivatives of glucocorticoids, estrogens, androgens and progestins or their respective antagonists.

In a currently preferred embodiment, it is the object of this invention to provide permanently charged agonists and antagonists for the clinical treatment of protracted angiogenesis and other diseases and pathological conditions. These anti-angiogenic anti-estrogens would possess estrogen antagonist activity, and may possess partial estrogen agonist or mixed activity, but would be limited in biodistribution by being permanently charged, thereby exhibiting reduced side effects and being beneficial for clinical use. Another object of this invention and clinical benefit is the comparatively rapid elimination from circulation of these agents due to the fact that they are not sequestered in fat itissue, thereby reducing toxicity and allowing for precise control of dosing. Yet another aspect of this invention is to provide for the formulation and drug delivery of the aforementioned anti-angiogenic anti-estrogen agents.

These and other objects of the present invention are achieved by providing compositions containing as an active ingredient a pharmaceutically effective amount of a compound of the general formula I:

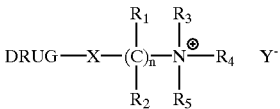

I wherein:
Y is a non-toxic pharmaceutically acceptable anion;
DRUG is a radical selected from the group consisting of a steroid agonist or antagonist, a mixed agonist-antagonist, and a partial agonist;
X is a direct bond or a radical selected from the group consisting of —O—; —NH—; —NR—, wherein R is an alkyl or aryl group with less than ten carbons; —PO$_3$—; —S—; —SO—; and —SO$_2$—;
R$_1$ and R$_2$ are the same or different and may be a radical selected from the group consisting of H, an alkyl of 1–10 carbon atoms, an arylalkyl of 7–16 carbons, and an aryl;
R$_3$, R$_4$ and R$_5$ are independently a radical selected from the group consisting of a branched or unbranched, cyclic or noncyclic, alkyl of 1–10 carbon atoms; an alkyl of up to 10 carbon atoms substituted by a carboxy, hydroxy, alkoxy, halo, or nitro group; a branched or unbranched, cyclic or noncyclic arylalkyl of 7–16 carbon atoms; and an aryl;
and n is 0–12.

Y may be exemplified by, but is not limited to, the following anions: phosphate, sulfate, chloride, bromide, iodide, an alkyl or aryl sulfonate, or an organic anion such as acetate, citrate or oxalate.

A more specific case and preferred embodiment of the general formula is:

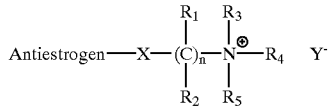

II wherein:
Y is a non-toxic pharmaceutically acceptable anion;
anti-estrogen is a radical selected from the group consisting of an estrogen antagonist, a mixed agonist-antagonist, and a partial agonist;
X is a direct bond or a radical selected from the group consisting of —O—; —NH—; —NR—, wherein R is an alkyl or aryl group with less than ten carbons; PO$_3$—; —S—; —SO—; and —SO$_2$—;
R$_1$ and R$_2$ are the same or different and may be a radical selected from the group consisting of H, an alkyl of 1–10 carbon atoms, an arylalkyl of 7–16 carbon atoms, and an aryl;
R$_3$, R$_4$ and R$_5$ are independently a radical selected from the group consisting of a branched or unbranched, cyclic or noncyclic alkyl of 1–10 carbon atoms; an alkyl of up to 10 carbon atoms substituted by a carboxy, hydroxy, alkoxy, halo, or nitro group; a branched or unbranched, cyclic or noncyclic arylalkyl of 7–16 carbon atoms; and an aryl;
and n is 0–12.

A most preferred embodiment according to the present invention comprises an anti-angiogenic compound of the general formula III:

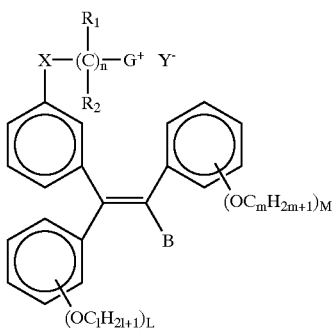

wherein
X is a direct bond or a radical selected from the group consisting of —O—, —NR—, —S—, —SO—, —SO$_2$—, and —PO$_3$—;
R, R$_1$ and R$_2$ are independently a radical selected from the group consisting of H, an alkyl of 1–10 carbon atoms; an aralkyl of 7–16 carbon atoms; and an aryl;
n is 0–12;
G is a cationic radical selected from the group consisting of —N(R')(R'')(R'''), —(O)N(R')(R''), —S(R')(R''), and —P(R')(R'')(R''');
R' is a radical selected from the group consisting of an alkyl of 1–10 carbon atoms; an alkyl of up to 10 carbon atoms substituted by a carboxy, hydroxy, alkoxy, halo, or nitro group; a cycloalkyl of 4–8 carbon atoms; a cycloalkyl-alkyl of 5–18 carbon atoms; and an aralkyl of 7–16 carbon atoms;
R'' and R''' are independently a radical selected from the group consisting of an alkyl of 1–7 carbon atoms and a 4- to 8-membered nitrogen containing ring;
B is a radical selected from the group consisting of an alkyl of 1–7 carbon atoms, a halogen, a nitrogen, and a moiety which is linked to the 2-position of the phenyl that is neither the phenyl linked to the same ethylene carbon as B, nor the phenyl substituted by the radical containing the permanently ionic group G, and which is selected from the group consisting of —CH$_2$C(R$_1$)(R$_2$)— and —CH$_2$—O—;
L and M are independently 0–3;
l and m are independently 1–7; and
Y is a pharmaceutically acceptable anion.

DETAILED DESCRIPTION OF THE INVENTION

Figure 1A:
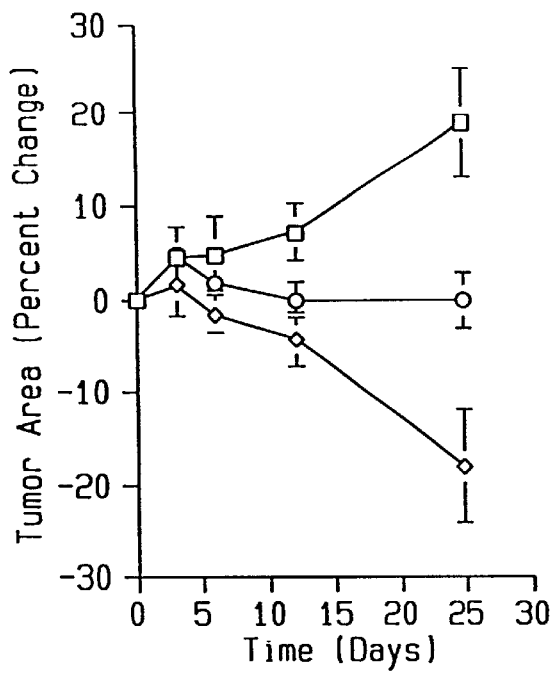
FIGS. 1A and 1B. Effects of estradiol, tamoxifen, TMI or a placebo on the growth of MCF-7 tumors implanted in the ventral fat pad of nude mice. The left panel gives data for tamoxifen, TMI and the placebo, while the right panel adds the group treated with estradiol.

The primary objective of the present invention is to provide effective compositions that provide anti-angiogenic activity in any disease or disorder where pathological angiogenesis is known to occur. Another objective of the present invention is to provide methods of treatment for the prevention or amelioration of such conditions, diseases and disorders using a composition containing a therapeutically effective amount of a permanently charged steroid agonist or antagonist. In currently preferred embodiments according to the present invention, it is now disclosed that permanently charged anti-estrogens may be used to prepare medicaments effective in the treatment of angiogenesis.

It is known that compounds designed as anti-estrogens may be effective anti-tumor agents even in estrogen receptor-negative tumors, thereby implicating additional mechanisms of action for these agents. A most preferred agent of the present invention would, therefore, be limited in its biodistribution, due to its permanent ionic nature, while simultaneously being efficacious (irrespective of the mechanisms involved).

Various classes of anti-estrogens can be used in accordance with the above-mentioned precepts. These include: (a) anti-estrogens derived from triphenylethylene, such as tamoxifen, toremifene and clomiphene; (b) anti-estrogens derived from diphenyl naphthalene, such as nafoxidine; and (c) anti-estrogens derived from triphenyl ethanol, such as ethamoxytriphetol.

The modification of drugs to form permanently charged derivatives may be most conveniently accomplished by the preparation of quaternary salts. Such compounds may be prepared by a variety of chemical reactions. In the case of anti-estrogens containing an amino group, one such method is to react the anti-estrogen with an alkylating agent. The alkylating agent can be an alkyl halide, tosylate, alkyl or dialkyl sulfate or any other appropriate moiety. The alkylation may be performed with or without addition of organic solvents, as appropriate, and may be carried out under cooling or at room temperature or with heating, as appropriate, to ensure that the reaction proceeds satisfactorily to completion. The reaction may be monitored by standard analytical methods known to one skilled in the art including thin layer chromatography, high pressure liquid chromatography, nuclear magnetic resonance spectroscopy or any other suitable method. The resulting quaternary salt may be purified by standard methods, known to the artisan, usually including at least one step involving recrystallization. The associated anion may be changed if desired by standard procedures such as ion-exchange columns.

Pharmacology

The compounds provided can be formulated by any required method to provide pharmaceutical compositions suitable for administration to a patient.

The novel compositions contain, in addition to the active ingredient, conventional pharmaceutically acceptable carriers, diluents and the like. Solid compositions for oral administration, such as tablets, pills, capsules or the like, may be prepared by mixing the active ingredient with conventional, pharmaceutically acceptable ingredients such as corn starch, lactose, sucrose, sorbitol, talc, stearic acid, magnesium stearate, dicalcium phosphate and gums, with pharmaceutically acceptable diluents. The tablets or pills can be coated or otherwise compounded with pharmaceutically acceptable materials known in the art to provide a dosage form affording prolonged action or sustained release. Other solid compositions can be prepared as microcapsules for parenteral administration. Liquid forms may be prepared for oral administration or for injection, the term including subcutaneous, intramuscular, intravenous, and other parenteral routes of administration. The liquid compositions include aqueous solutions (with or without organic cosolvents), aqueous or oil suspensions, emulsions with edible oils, as well as similar pharmaceutical vehicles. In addition, the compositions of the present invention may be formed as encapsulated pellets or other depots, for sustained delivery.

The active dose for humans is generally in the range of from 0.01 mg to about 10 mg per kg body weight, in a regimen of 1–4 times a day. However, administration at longer intervals may also be possible, for compounds or formulations having prolonged action.

The preferred range of dosage is from 0.05 to 5 mg per kg body weight. It is evident to one skilled in the art that the dosage form and regimen would be determined by the attending physician, according to the disease to be treated, the method of administration, and the patient's general condition. It will be appreciated that the most appropriate form of administration of the pharmaceutical compositions of the present invention will depend first and foremost on the clinical indication being treated. The prophylactic treatment of a healthy individual at high risk for pathological angiogenesis will necessitate a sustained maintenance dosage regimen. This type of treatment might be applied to individuals at risk for diabetic retinopathy, retinopathy of prematurity, macular degeneration and other conditions that are known to afflict particular sets of patients. In contradistinction, the treatment of an existing disease might require higher doses at more frequent intervals. It is further anticipated that the treatment of certain conditions known to involve abnormal vascular smooth muscle cell proliferation, including restenosis, will be treated beneficially with compositions according to the present invention.

Biological Activity

The present invention provides novel medical uses for both certain known compounds as disclosed in WO 95/25720 and for additional steroid agonists and antagonists of the general formula I as described above. Certain charged derivatives of tamoxifen have been shown to possess improved anti-tumor activity when compared to tamoxifen. It is now disclosed that these derivatives display potent anti-angiogenic activity even in systems where tamoxifen itself is devoid of activity.

To assess potential mechanisms of action, the tamoxifen analogs, tamoxifen methiodide (TMI), tamoxifen benzyl bromide (TBB) and tamoxifen itself were examined in various biochemical assays related to angiogenesis. Blood vessel formation and destruction involves a series of events in which the basement membranes of existing vessels degrade, followed by endothelial cell migration, proliferation and re-establishment of the basement membrane. Thus, the effect of TMI on the ability of bovine endothelial cell to assemble into tubes and elongate when seeded in a basement membrane preparation (Matrigel) was evaluated. Furthermore, since angiogenesis involves degradation of basement membrane proteins (including type IV collagen), the efficacy of TMI, TBB and tamoxifen in blocking matrix metalloprotease activity was examined through zymography using both whole cell (human fibrosarcoma and bovine endothelial cells) and cell-free systems. Finally, the specific action of TMI on transcription of various collagenases was investigated.

In order to further illustrate the present invention, specific examples are given below. It is to be understood that the examples given are for illustration only and are in no way limiting.

EXAMPLES

Methods of Evaluation

Chemistry

Tamoxifen methiodide was prepared by reacting 2.0 g of tamoxifen (Aldrich Chemical Co., St. Louis, Mo.) with methyl iodide at 0° C. for 24 hours. Ethyl acetate was then added to afford a white precipitate, which was recrystallized from methanol to yield >99% tamoxifen methiodide. Tamoxifen benzyl bromide was synthesized by reacting tamoxifen with benzyl bromide.

Chemical Structures

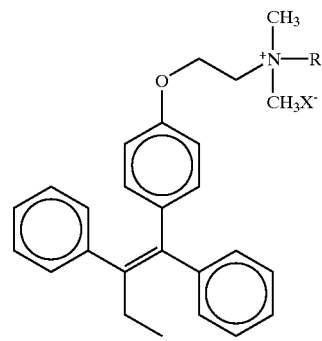

TMI: $CH_3$, X = I
TBzBr: R = $CH_2C_6H_5$, X = B

Cell Cultures

HT-1080 cells (CCL 121), derived from a metastatic lesion of a human fibrosarcoma and primary bovine endothelial cells were obtained from the American Type Culture collection (Rockville, Md.). Cells were maintained under an atmosphere of 5% $CO_2$, in Dulbecco's Minimal Essential Medium (DMEM) supplemented with 10% fetal calf serum, glutamine, vitamins, non-essential amino acids and antibiotics (Biological Industries, Kibbutz Beth HaEmek, Israel).

Analysis of Collagenase IV Expression

Regulation of collagenase gene expression (for MMP-2 and MMP-9) was studied by measuring the activation of the relevant promoters linked to chloramphenicol acetyl transferase (CAT) as a reporter gene. The relevant vectors were introduced into the fibrosarcoma and endothelial cells by the lipofection as indicated by the manufacturer. CAT activity was determined after 3, 6 and 24 hrs either in the absence or presence of various concentrations of TMI.

Analysis of Collagenase Activity in Cell Systems

Sub-confluent cell cultures were incubated for 6 to 24 hours in serum-free DMEM, either with or without various concentrations of TMI or tamoxifen, and the resultant supernatant was analyzed for collagenolytic activity. The collagenolytic activity was determined using a gelatin-impregnated (1 mg/ml, Difco, Detroit Mich.) SDS-PAGE 8% gel, as previously described, with minor modifications. Briefly, the culture media samples were separated on the substrate-impregnated gels under non-reducing conditions, followed by 30 min of incubation of 2.5% Triton X-100 (BDH, UK). The gels were then incubated for 16 hours at 37° C. in 50 mM TRIS, 0.2 M NaCl, 5 mM $CaCl_2$, 0.02% BRIJ 35 (w/v) at pH 7.6. At the end of the incubation period, the gels were stained with 0.5% Coomassie G 250 (Bio-Rad, Richmond, Calif.) in methanol/acetic acid/$H_2O$ (30:10:60). The intensity of the stained bands was then determined using a computerized densitometer (Molecular Dynamics Model 300A).

Analysis of Collagenase Activity in Cell-Free Systems

Endothelial Cell Tube Formation

Bovine endothelial cells were harvested by brief exposure to 1 mM EDTA, washed with DMEM containing 0.1% bovine serum albumin and added to a layer of Matrigel (basement membrane components) in a 24 well plate to a density of 50,000 cells per well. After attachment, culture media (1.0 ml) was added and the plates incubated as a monolayer culture in the presence or absence of various concentrations of TMI. The plates were analyzed hourly using Hoffman optics for endothelial tube formation and growth. Photomicrographs were taken for estimation of relative inhibitory action.

Animal Evaluation

Female CD1-nu/nu athymic mice (6 weeks old) were obtained from the Weizmann Institute Department of Animal Services. MCF-7 cells, serially passed as described above, were detached from the culturing flasks with 0.03% EDTA in phosphate buffered saline (PBS) and washed several times in normal saline. Cells ($10^7$/innoculum) were then injected into the ventral fat pad at the level of the breast. Coincident with cell introduction, a slow-release pellet of estradiol (0.72 mg/pellet, 45-day release profile; Innovative Research, Sarasota, Fla.) was implanted subcutaneously in the flank of the animal. Mice were anesthetized with ketamine/Rompun (i.p.) for the surgical procedures. Within 3–6 weeks, solid tumors were observed in all animals attaining an average size of approximately 1 $cm^3$. At this point, animals were randomized into four study groups. In the first, the estrogen pellet was removed and replaced with a slow-release TMI-laden pellet (6.3 mg, 45-day release) (n=5). In the second group, the estrogen pellet was removed and replaced with a tamoxifen pellet (n=7). The third group was treated with a blank (placebo) pellet (n=5), while the fourth group was reimplanted with an estradiol pellet (n=4). TMI and placebo-treated animals were imaged (under ketamine/Rompun anesthesia) either immediately before pellet exchange (day 0) or at day 3, 6, 12 and 25 after pellet exchange.

NMR Measurements

MRI images were recorded with a Bruker 4.7 (tesla)/30 Biospec spectrometer (Bruker Medizintechnik, Rheinstetten, Germany). 1H Spin-echo images were recorded at 200.12 MHz using a custom-made 4.5 cm rf coil with an image data matrix of 256×128 pixels. Pilot scans of the tumors were completed using a fast transverse multi-slice spin-echo sequence (giving T1-weighted spectra; inter-echo time (TE)=16 msec, recovery time (TR)=500 msec) followed by T2-weighted sequences in which axial slices perpendicular to the spine (i.e., a coronal orientation) were recorded. In the latter case, spin-echo images were obtained using a 4 cm field of view, 1 mm slice thickness, 1.2 mm slice-to-slice distance and a four-sequence average. The TE and TR were optimized to provide the best image contrast generating values of 80 and 3200 msec, respectively. This gave a total imaging time of approximately 30 min. Under the conditions reported, the in-plane resolution was 155×310 $\mu$m. Tumor size was calculated using a slice-to-slice reconstruction in which the slice surface area was obtained from histograms provided by the resident Bruker software package using the following relationship:

$$Volume\ (cm^3) = \Sigma XSA \cdot (l+ssd) + \Sigma ES \cdot (l+ssd/2)$$

where XSA is the cross-sectional area of an internal slice, ES is the cross-sectional area of an edge slice, l is the slice thickness and ssd is the distance from the middle of one slice to the middle of the next. For image analysis, the average pixel intensity of viable portions of MCF-7 tumors was determined from a central tumor slice using histograms generated by the dedicated Bruker software package. Necrosis and fibrosis were estimated using pixel by pixel analysis, with necrosis defined as areas demonstrating an increase in intensity of 25% over viable areas. Fibrosis was defined as those areas manifesting a decrease in pixel intensity of $^350\%$.

Histology

Tumors from TMI-treated animals and from placebo-treated animals were removed after cervical dislocation. Tumors were treated with a biological dye (Davidson Marking Systems, Bradley Products, Bloomington, Minn.) so that histological sections could be oriented in the same direction as MRI slice images. The histological plane corresponding to the central slice of the MRI study was established by a single cut through the tumor. This plane was based on the position of the tumor in the spectrometer, sagittal, transverse and coronal images and anatomical landmarks. The bisected tumors were fixed in 10% formalin, dehydrated in 70% ethanol, blocked in paraffin. 4 $\mu$m histological sections were cut, placed on slides and stained with either hematoxylin-eosin or a modified trichrome method. Hematoxylin-eosin was used to assess viability, necrosis and pigmentation. The modified trichrome method was applied to the identification of fibrotic regions (i.e., the dye stains for mucopolysaccharides).

Vascular density was determined using two techniques: by morphometric analysis of histological sections and by image analysis of GSL-1 lectin stained sections. For microscopic analysis, 4 $\mu$m tumor sections were stained with a modified Trichrome method. A 1 cm grid divided into 100 squares was placed in the eyepiece. At the magnification used (400×), the grid covered an area 250 $\mu m^2$ and each grid square represented 25 $\mu m^2$. In each field, the number of grid squares containing capillaries, as defined by either the presence of red blood cells or a distinct endothelial cell, were recorded. Two sets of analyses were completed: (1) an examination of the entire tumor; and (2) an evaluation of viable areas. In the latter case, three meridians were constructed, oriented perpendicular to the long axis of the section. Starting just within the tumor-capsule interface, vascular density determinations were made every mm until the opposite edge of the tumor was reached. A minimum of three meridians (i.e., nine measurements/mm/tumor) were performed. For analysis of viable tissue, areas of highest vascularity were considered as previously outlined, with 8–12 fields per tumor being examined. In addition, endothelial cytology was noted.

For specific staining of endothelial cells, paraffin-embedded sections (4 μm) were deparafinized and rehydrated. Sections were first treated with a blocking solution containing nonimmune goat serum for 30 min at room temperature and then with a 0.1 mg/ml solution of biotinylated Griffonia simplicifolia lectin (GSL-1) for 60 min. The GSL-1 lectin binds specifically to α-galactosyl residues and marks the vascular endothelium in mice. The sections were then washed with TRIS buffered saline (TBS) and treated for 30 min with avidin-biotin-peroxidase complex (Vector Laboratories, Burlingame, Calif.), after which the peroxidase was activated by incubation of the sections with 0.1 M acetate buffer (pH 5.2) containing 3% $H_2O_2$ and 3% 3-amino-9-ethylcarbazole for 5–10 min. The sections were then washed with distilled water, counterstained with hematoxylin, dehydrated and mounted on a coverslip with permount. Image analysis of the stained sections was completed using a GALAI CUE-2 system with a 50× objective. All sections were scanned for regions of highest staining which were selected for measurement. The area of stained endothelial cells was determined by measuring the area above a threshold intensity (red 46–165; green 25–119; blue 37–94) of the peroxidase reaction product in each slice. The ratio of the stained area to the area viewed gave an average endothelial density within an experimental error of 5%. Ten to fifteen areas per section were recorded for tumors treated three days with either the placebo and TMI.

Results of Evaluation

Magnetic resonance imaging (MRI) of breast tumors allows a non-invasive assessment of the effects of drug treatment on tumor pathomorphology. This tool was applied to examine the effect of TMI on an implanted human breast tumor in athymic nude mice. In addition to the TMI-treated animals, three control groups were included in this study, specifically: (1) a group of animals in which the supportive estrogen pellet was removed and replaced with a placebo pellet; (2) a group in which the estrogen pellet was replaced with a second estrogen pellet; and (3) a group in which the estrogen pellet was replaced with a tamoxifen-laden pellet. In this study, the breast tumor was implanted at the level of the milk line in the ventral fat pat. This paradigm was followed since it appears to be more representative of the human condition than the standard flank implanted model. Tumors generated by implantation of tumor cells in the breast do manifest differences from the flank-implanted model including a faster growth rate and a higher tolerance to the effects of tamoxifen.

Analysis of MR images over time with subsequent reconstruction of tumor slices indicated that estrogen-treated controls manifested a rapid growth rate wherein tumors more than doubled in size over the 25 day time course. Placebo-treated tumors also grew relative to day 0 values but at a much slower pace, increasing in size by about 20%. The reduction in the growth rate is due to partial hormonal ablation. Tamoxifen was tumoristatic in this study with day 25 results essentially the same as day 0 tumor dimensions. TMI induced tumor regression, with the MCF-7 neoplasms shrinking an average of 20% over the 25 day time course. The effects of the anti-estrogens was not solely due to removal of the estrogen pellet since tumors implanted in placebo-treated animals continued to grow over time. This data confirmed the data obtained previously in a flank-implanted model (FIG. 1).

Figure 1B:
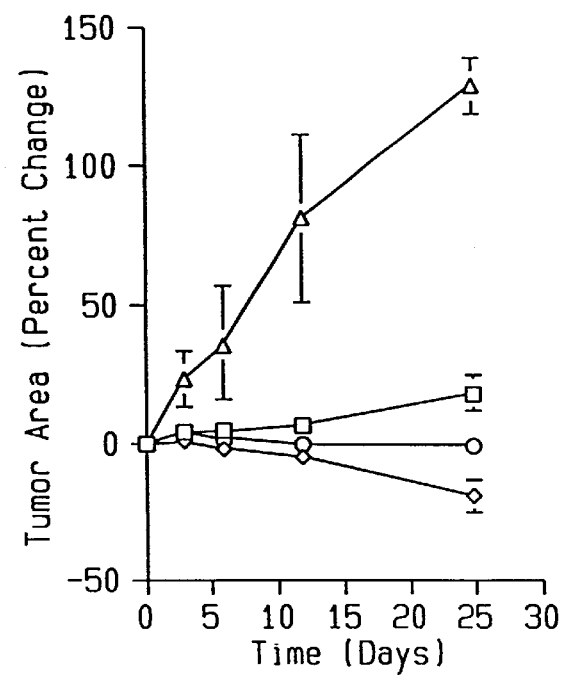

FIG. 1 shows the effect of estradiol (n=4), tamoxifen (n=7), TMI (n=5) or the placebo (n=5) on the growth of MCF-7 tumors implanted in the ventral fat pad of nude mice. The left panel gives data for tamoxifen, TMI and the placebo, while the right panel adds the data from the estradiol group. Drugs were administered as slow-release pellets implanted (s.c.) in the flank.

Figure 2:
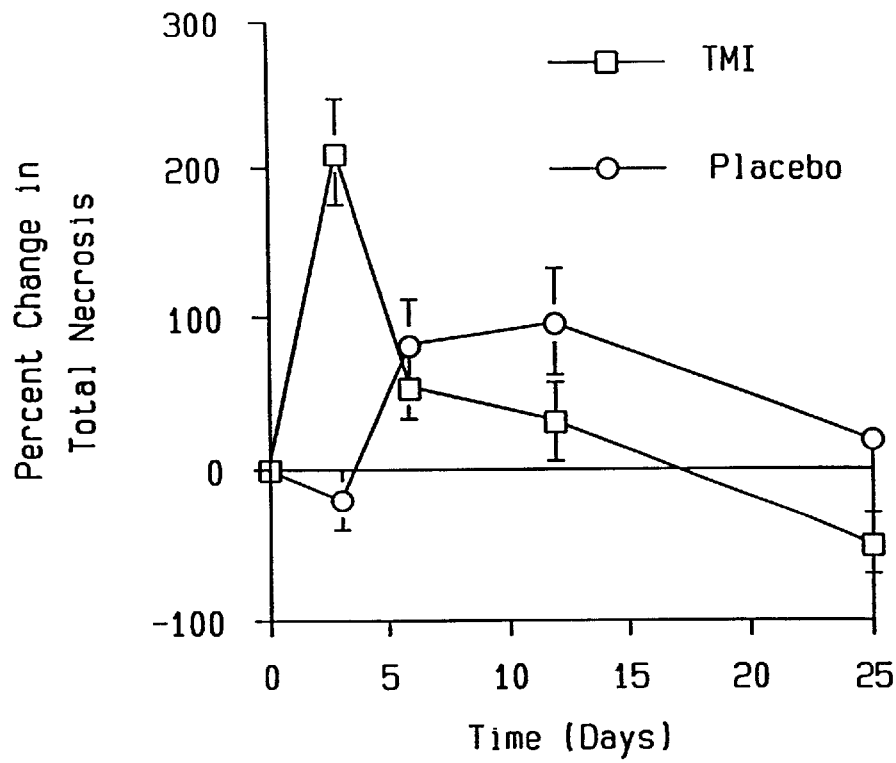
FIG. 2. Percent change in total necrosis relative to day 0 induced by TMI or placebo in MCF-7 human breast tumors implanted in nude mice.

In vivo tumor histology was assessed for TMI and placebo-treated tumors using T2-weighted MR images. Using tools developed for the assessment of the effects of tamoxifen and estradiol treatment, comparisons of the histological sections and TMI/placebo images indicated that: (1) viable tumor areas appeared gray (intermediate intensity) in the T2-weighted spin-echo images; (2) necrotic areas appeared white (hyperintense), due mainly to longer spin-spin relaxation times with some contribution of increased proton density (i.e., higher water content); and (3) fibrotic areas appeared dark (hypointense), due to shorter spin-spin relaxation times and lower water content. According to these definitions, placebo administration did not result in a significant change in tumor necrosis by day 3 but did cause an increase in necrosis by day 6 (FIG. 2). At this time, the area of necrosis was two-fold higher than that observed on day 0 (increasing from an average of 20% to approximately 40%). FIG. 2 shows the percent change in total necrosis relative to day 0 induced by TMI or the placebo in MCF-7 human breast tumors implanted in nude mice.

Treatment of tumors with TMI provoked a different response in several respects. The initiation of tumor-wide necrosis occurred at the first sampling point (day 3) rather than at day 6, as in the case of the placebo. In addition, the total area of necrosis increased almost three-fold from a day 0 average of approximately 25% to a day three average of 72%. All of these initial changes in tumor structure occurred before any significant change in tumor size had become apparent. In both TMI- and placebo-treatments, regression of necrosis was associated with fibrotic infiltration. Histological analysis of the resected tumors correlated well with the MRI descriptions.

TMI induces tumor necrosis that manifests a faster onset and which is more extensive than that induced by partial estrogen ablation (i.e., removal of the estrogen pellet). In addition to the effects on tumor size, preliminary studies also suggest that TMI is more potent than tamoxifen in the induction of necrosis. Thus, tamoxifen, similar to TMI, was found to induce rapid necrosis (by day 3) as assessed by MRI, but the maximum extent of necrosis was 50% (compared to 72% for TMI). Importantly, a portion of the tumors treated with tamoxifen became tolerant to the effects of the drug and began to regrow over time. This phenomenon did not occur with TMI.

Figure 3:
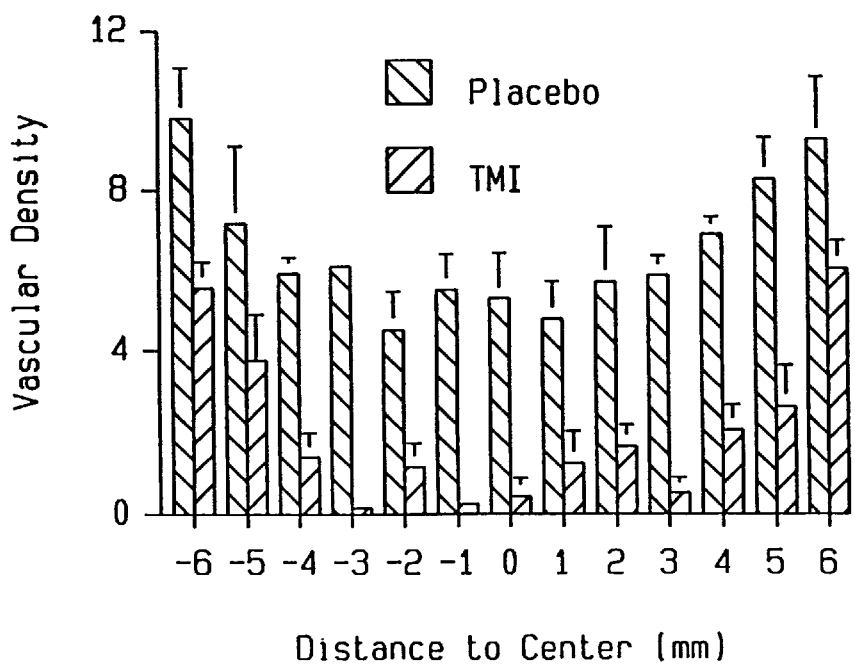
FIG. 3. Capillary density in MCF-7 tumors implanted into nude mice after placebo or TMI treatment (n=5 tumors/group). All differences were significant with the exception of (−5 mm) and (6 mm).

In the case of tamoxifen, the speed with which necrosis occurs, and the finding that the number of capillaries in the tumor is reduced, has led to the proposition that tamoxifen exerts in vivo anti-angiogenic action resulting in tumor starvation and the observed cell death (Furman-Haran et al., Cancer Res. 54, 5511–5514, 1994). To see if TMI shared these effects, vascular density was determined in TMI and placebo-treated tumor sections using two techniques: microscopic morphometry and immuno-staining. Morphometric vascular area was determined using a modification of a histological grading system described by Brem et al. (JNCI, 48, 347–356, 1972). In this approach the percentage of various microscopic fields (250 $\mu m^2$ grid) containing capillaries (as defined by either red blood cells or distinct endothelial cells) was estimated (FIG. 3).

Figure 4:
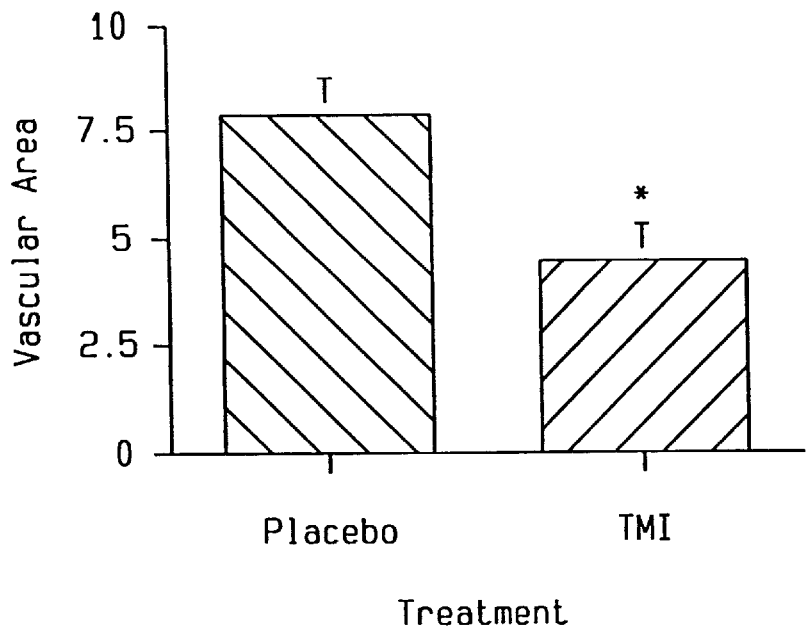
FIG. 4. Capillary density in viable areas of MCF-7 tumors implanted into nude mice after placebo or TMI treatment (n=5 tumors/group).

This was completed both for the tumors as a whole as well as for viable regions within tumors. The density of capillaries was found to be reduced upon TMI exposure. In evaluations of whole tumors, the tumor capsules were invariably highly vascular, but the density fell off considerably just within this interface. Areas of necrosis were generally devoid of blood vessels. Since TMI induced a higher extent of necrosis compared to placebo-treated tumors, it is not surprising that these neoplasms would manifest lower overall vascular densities. When, however, the analysis was restricted only to viable regions, there was a significant reduction in vascularization after TMI treatment, with a reduction in capillary area by 50% compared with the placebo (FIG. 4). In addition to vascular count and area, endothelial cytology and abnormalities thereof were noted. Cytological anomalies which were noted and recorded included: plump nuclei, plump nuclei with prominent nucleolus, hyperchromatic nuclei and mitotic figures.

Figure 5:
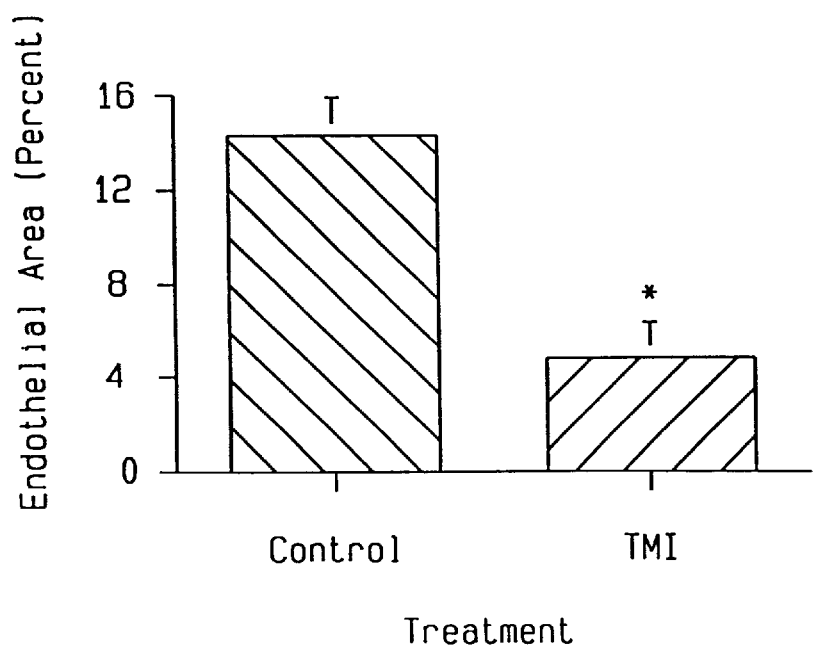
FIG. 5. Effect of TMI on endothelial cell area in GSL-1 labeled tumor sections. Animals were treated for three days with TMI or with a placebo pellet.

Vascular density of murine endothelial cells was evaluated by specific staining, using the GSL-1 lectin (the equivalent of factor VIII antibody staining for human endothelial systems) followed by color image analysis of the resulting sections. The mean percentage of endothelial cell areas in viable regions of control tumors was 14% and in viable areas of TMI treated tumors was 5%. The three-fold reduction in endothelial cells density was highly significant (FIG. 5). These two events, reduced vascular area and endothelial density and the concomitant increase in tumor necrosis, are highly supportive of the hypothesis that TMI induces cytocidal activity through a reduction in the number of blood vessels resulting in tumor starvation.

Preliminary data on TBB in the MCF-7 model have also been generated. Like TMI, the TBB was well tolerated in mice with doses as high as 10 mg/Kg provoking no adverse effects when given daily over a two week time course. Administration of TBB to MCF-7 tumor-bearing mice caused significant tumor regression that amounted to 32% over two weeks of daily dosing. TMI induced a 20% regression over a 25 day time course. This data would suggest that TBB is even more potent in its anticancer properties than tamoxifen methiodide.

The action of TMI on angiogenesis was evaluated using in vitro techniques. Bovine endothelial cells seeded on matrigel (a basement membrane preparation made up of laminin, collagen type IV, heparin sulfate proteoglycan and entactin) will form tubes which elongate as a function of time. TMI inhibited tube formation and growth in a concentration-dependent manner over a dose range from 1 to 20 $\mu$M. A dose of 10 $\mu$M of TMI decreased tube area by more than 70%, as measured by image analysis.

Figure 6A:
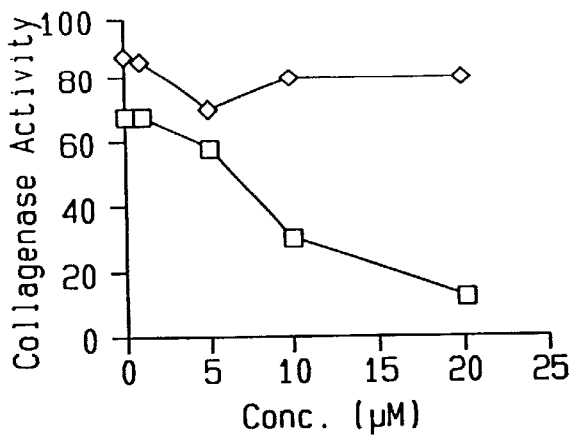
FIGS. 6A and 6B. Effect of Tamoxifen or TMI on Gelatinase A activity (72 kDa isoform system) determined at 6 hours (left) or 24 hours (right) after exposure of cells.
Figure 6B:
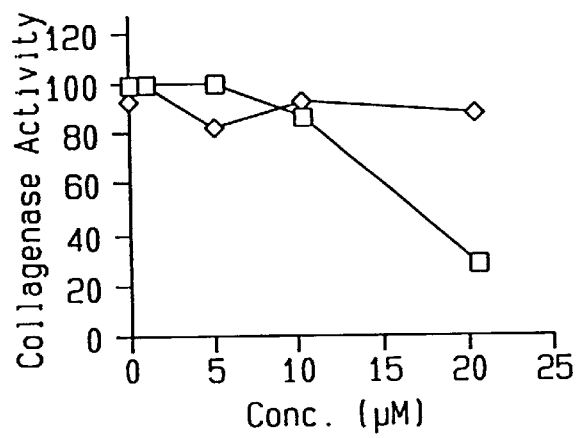
Figure 7:
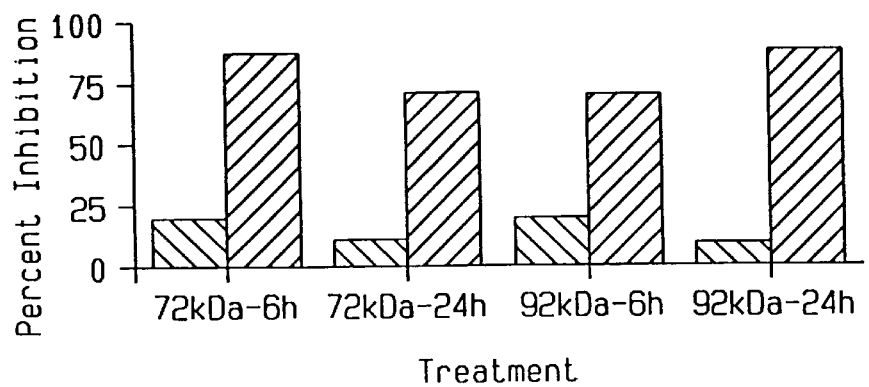
FIG. 7. Effect of 20 μM Tamoxifen or TMI on collagenase activity for both the 72 kDa and 92 kDa isoform systems determined using zymography at 6 and 24 hours after drug administration.

The effect of TMI relative to tamoxifen on collagenase activity was considered in both whole cell and cell-free systems. Human fibrosarcoma cells were plated in culture and exposed to either TMI or tamoxifen at doses ranging from 0.5 to 20 $\mu$M. After 6 and 24 hours of incubation, samples of supernatant were withdrawn and assayed for collagenolytic activity associated with two collagenase isozymes (gelatinase A and B (MMP-2 and MMP-9)) by zymography (substrate impregnated non-reducing activity gels). TMI inhibited both isozymes in a dose-dependent manner, with complete inhibition observed at the 20 $\mu$M level (FIGS. 6 and 7). Tamoxifen, on the other hand, demonstrated no significant inhibitory activity at doses up to and including 20 $\mu$M.

Figure 8:
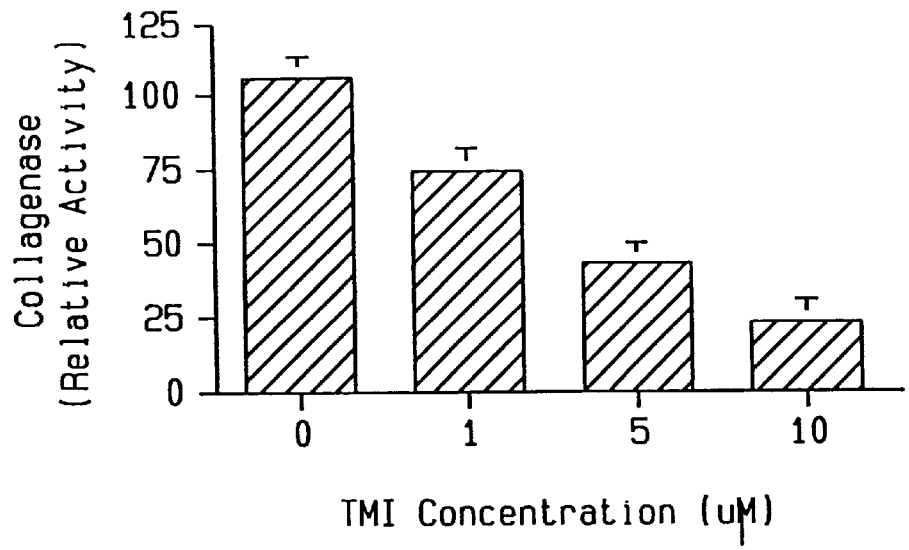
FIG. 8. Effect of TMI on Gelatinase A activity in bovine endothelial cells.

FIG. 7 shows the effect of 20 $\mu$M tamoxifen or TMI on collagenase activity for both the 72 kDa and 92 kDa isoform systems, as determined by zymography at 6 and 24 hours after drug administration. In addition, TMI proved to be a potent inhibitor of collagenase (gelatinase A) activity in bovine endothelial cells with an $IC_{50}$ of between 1 and 5 $\mu$M (FIG. 8).

Figure 9:
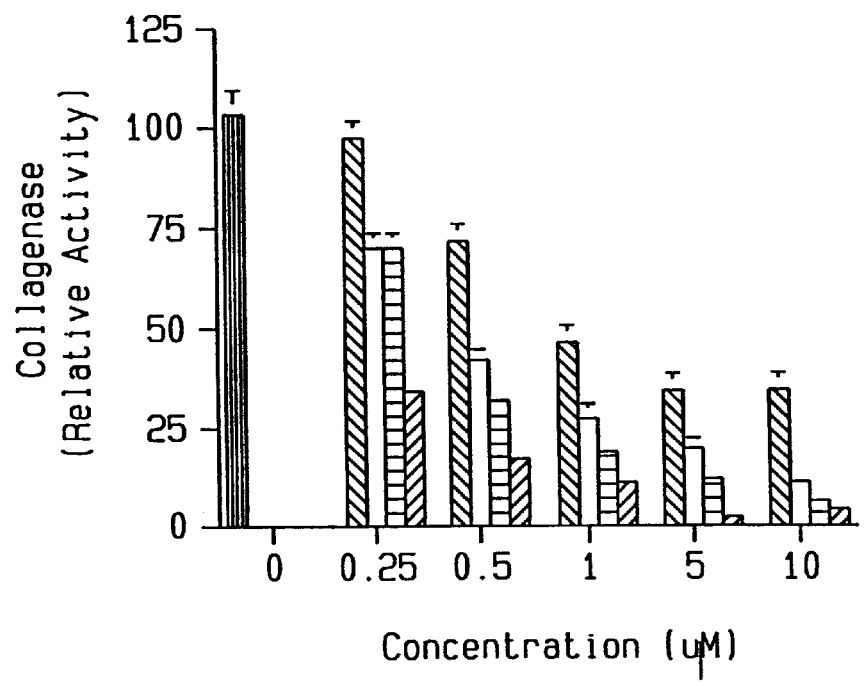
FIG. 9. Effect of TMI or TBB on collagenolytic activity (Gelatinase A, MMP-2 and Gelatinase B, MMP-9) in human fibrosarcoma cells (HT-1018).

TBB was also examined in this assay and directly compared with TMI. TBB was more potent than TMI as an inhibitor of both the 72 kDa (gelatinase A, MMP-2) and 92 kDa (gelatinase B, MMP-9) isoforms of collagenase (FIG. 9).

In cell free systems, TMI was evaluated to determine whether the inhibitory effects were manifested at the level of the enzyme or at other loci. There was no effect of TMI on enzymatic activity at any concentration examined. This data suggests that TMI inhibits gelatinase A and B biosynthesis and or gene expression in the concentration range tested.

Figure 10:
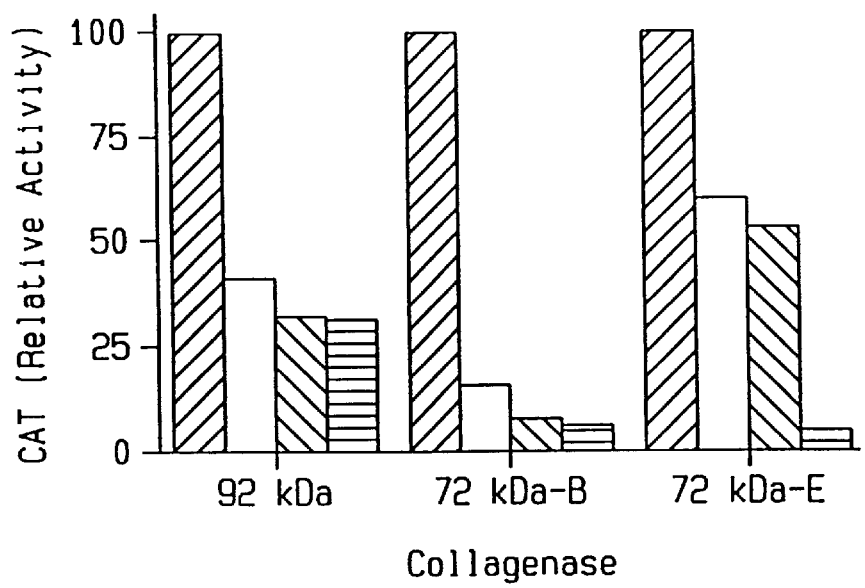
FIG. 10. Effect of TMI on the MMP-2 (Gelatinase A) related CAT activity in transfected bovine endothelial cells.

To further examine where the inhibitory effects of TMI are manifested, human fibrosarcoma cells as well as bovine endothelial cells were transfected with plasmids containing the promoters for type IV collagenase (both MMP-2 and MMP-9) and the chloramphenicol acetyl transferase (CAT) construct to act as a reporter. Simian virus-40 (SV-40) served as the positive control. TMI was added to the transfected cells at concentrations of 1, 5 and 10 $\mu$M for 2 days, at which time cell viability was confirmed by trypan blue exclusion and cell counting. In fibrosarcoma cells, TMI was found to inhibit transcription directed by promoters of both isozymes in a dose-dependent manner, with even the lowest dose of TMI exerting significant inhibitory action (FIG. 10). FIG. 10 shows the effect of TMI at concentrations of 1, 5 and 10 $\mu$M on CAT activity expressed in a cell system transfected with plasmids containing the promoters for the 92 kDa isoform of collagenase (634 base-pair promoter) or the 72 kDa isoform of collagenase (basic promoter—B or promoter plus enhancer—E).

Figure 11:
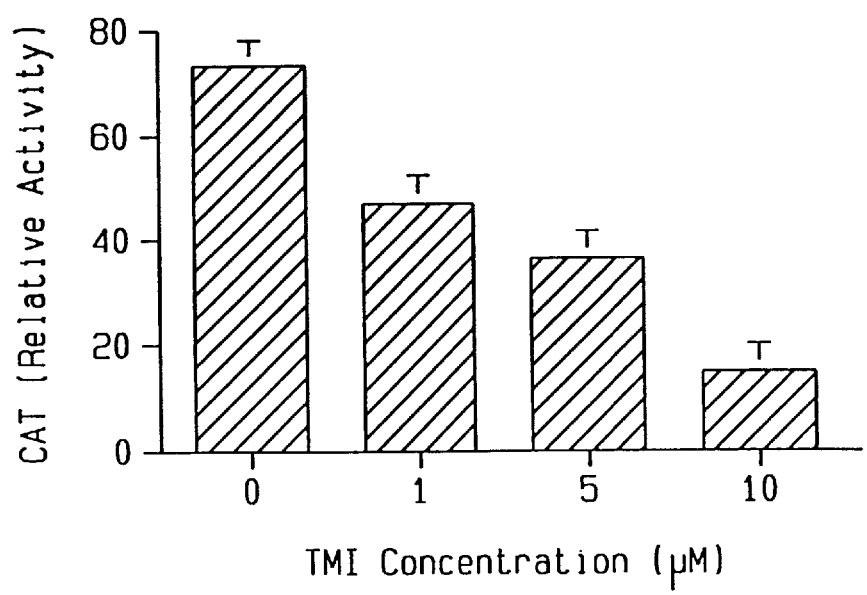
FIG. 11. Effect of TMI on the MMP-2 (Gelatinase A) related CAT activity in transfected bovine endothelial cells.

In endothelial cells, TMI reduced CAT activity by 45% at 1.0 $\mu$M and by 80% at 10 $\mu$M. This data suggests that the action of TMI on expression of collagenases is germane to vascular systems (FIG. 11).

Conclusions

1. For TMI, a decrease in vascular density was produced in both total tumor area as well as viable regions, as measured by morphometry and endothelial cell-specific staining.

2. TMI is an inhibitor of MMP-2 in bovine endothelial cells and MMP-2/MMP-9 in human fibrosarcoma cell lines.

3. TBB is more potent than TMI in the inhibition of metalloproteases in the systems examined.

4. Studies in transfected CAT systems in both fibrosarcoma and endothelial cells indicate that TMI inhibits matrix metalloproteases at the level of biosynthesis or expression. Furthermore, the lack of activity of the tamoxifen analog in cell free systems indicates that TMI does not directly inhibit the enzymes.

TMI and TBB, therefore, exert potent anti-angiogenic action which appears to be correlated with their ability to suppress transcription or expression of metalloproteases.

While the invention has been described in terms of various preferred embodiments, the skilled artisan will appreciate that various modifications, substitutions, omissions and changes may be made without departing from the spirit thereof. Accordingly, it is not intended that the scope of the present invention be limited solely by the scope of the following claims.

What is claimed is:

1. A method for treating a medical condition which involves angiogenesis in a subject, which comprises administering to a subject in need of such treatment a therapeutically effective amount of a pharmaceutical composition having anti-angiogenic activity which contains as an active ingredient a therapeutically effective quantity of a compound of the formula (I):

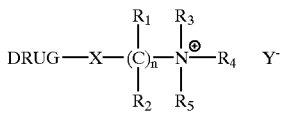

wherein:

Y is a non-toxic pharmaceutically acceptable anion;

DRUG is a radical selected from the group consisting of a steroid agonist or antagonist, a mixed agonist-antagonist, and a partial agonist;

X is a direct bond or a radical selected from the group consisting of —O—; —NH—; —NR—, wherein R is an alkyl or aryl group with less than ten carbons; —$PO_3$—; —S—; —SO—; and —$SO_2$—;

$R_1$ and $R_2$ are the same or different and may be a radical selected from the group consisting of H, an alkyl of 1–10 carbon atoms, an arylalkyl of 7–16 carbons, and an aryl;

$R_3$, $R_4$ and $R_5$ are independently a radical selected from the group consisting of a branched or unbranched, cyclic or noncyclic, alkyl of 1–10 carbon atoms; an alkyl of up to 10 carbon atoms substituted by a carboxy, hydroxy, alkoxy, halo, or nitro group; a branched or unbranched, cyclic or noncyclic arylalkyl of 7–16 carbon atoms; and an aryl; and n is 0–12.

2. The method of claim 1 wherein the pharmaceutical composition includes a pharmaceutically acceptable carrier or diluent.

3. The method of claim 2 wherein the pharmaceutical composition includes a dose of the compound of formula I in the range of from 0.01 mg to about 10 mg per kg body weight of the subject.

4. The method of claim 1 wherein the compound of formula I is tamoxifen benzyl bromide or tamoxifen methiodide.

5. The method of claim 1 wherein the DRUG does not include a triphenyl ethyl or triphenyl ethylene moiety in which the ethyl or ethylene moieties are not additionally substituted.

6. The method of claim 1 wherein Y is an anion selected from the group consisting of a phosphate, sulfate, chloride, bromide, iodide, and an organic anion.

7. The method of claim 1 wherein the compound has the formula:

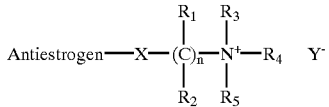

wherein:

Y is a non-toxic pharmaceutically acceptable anion;

Anti-estrogen is a radical selected from the group consisting of an estrogen agonist, and estrogen antagonist, a mixed agonist-antagonist, and a partial agonist;

X is a direct bond or a radical selected from the group consisting of —O—; —NH—; —NR—, wherein R is an alkyl or aryl group with less than ten carbons; —$PO_3$—; —S—; —SO—; and —$SO_2$—;

$R_1$ and $R_2$ are the same or different and may be a radical selected from the group consisting of H, an alkyl of 1–10 carbon atoms, an arylalkyl of 7–16 carbons, and an aryl;

$R_3$, $R_4$ and $R_5$ are independently a radical selected from the group consisting of a branched or unbranched, cyclic or noncyclic, alkyl of 1–10 carbon atoms; an alkyl of up to 10 carbon atoms substituted by a carboxy, hydroxy, alkoxy, halo, or nitro group; a branched or unbranched, cyclic or noncyclic arylalkyl of 7–16 carbon atoms; and an aryl; and n is 0–12.

8. The method of claim 7 wherein the pharmaceutical composition includes a pharmaceutically acceptable carrier or diluent.

9. The method of claim 8 wherein the pharmaceutical composition includes a dose of the compound in the range of from 0.01 mg to about 10 mg per kg body weight of the subject.

10. The method of claim 7 wherein the Antiestrogen does not include a triphenyl ethyl or triphenyl ethylene moiety in which the ethyl or ethylene moieties are not additionally substituted.

11. The method of claim 7 wherein Y is an anion selected from the group consisting of a phosphate, sulfate, chloride, bromide, iodide, and an organic anion.

12. The method of claim 1 wherein the compound has the formula:

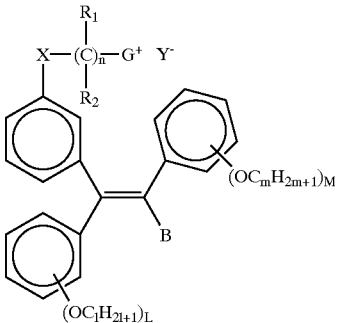

wherein:

X is a direct bond or a radical selected from the group consisting of —O—, —NR—, —S—, —SO—, —$SO_2$—, and —$PO_3$—;

R, $R_1$ and $R_2$ are independently a radical selected from the group consisting of H, an alkyl of 1–10 carbon atoms; an aralkyl of 7–16 carbon atoms; and an aryl;

n is 0–12;

G is a cationic radical selected from the group consisting of —N(R')(R")(R'''), —(O)N(R')(R"), —S(R')(R"), and —P(R')(R")(R''');

R' is a radical selected from the group consisting of an alkyl of 1–10 carbon atoms; an alkyl of up to 10 carbon atoms substituted by a carboxy, hydroxy, alkoxy, halo, or nitro group; a cycloalkyl of 4–8 carbon atoms; a cycloalkyl-alkyl of 5–18 carbon atoms; and an aralkyl of 7–16 carbon atoms;

R" and R''' are independently a radical selected from the group consisting of an alkyl of 1–7 carbon atoms and a 4- to 8-membered nitrogen containing ring;

B is a radical selected from the group consisting of an alkyl of 1–7 carbon atoms, a halogen, a nitrogen, and a moiety which is linked to the 2-position of the phenyl that is neither the phenyl linked to the same ethylene carbon as B, nor the phenyl substituted by the radical containing the permanently ionic group G, and which is selected from the group consisting of —$CH_2C(R_1)(R_2)$— and —$CH_2$—O—;

L and M are independently 0–3;

l and m are independently 1–7; and

Y is a pharmaceutically acceptable anion.

13. The method of claim 12 wherein the pharmaceutical composition includes a pharmaceutically acceptable carrier or diluent.

14. The method of claim 13 wherein the pharmaceutical composition includes a dose of the compound in the range of from 0.01 mg to about 10 mg per kg body weight of the subject.

15. The method of claim 12 wherein Y is an anion selected from the group consisting of a phosphate, sulfate, chloride, bromide, iodide, and an organic anion and wherein the compound does not include a triphenyl ethyl or triphenyl ethylene moiety in which the ethyl or ethylene moieties are not additionally substituted.

16. The method of claim 1 wherein the condition is selected from the group consisting of restenosis, arthritis, psoriasis, diabetic retinopathy, retinopathy of prematurity, macular degeneration, scleroderma, hemangioma, retrolental fibroplasia, abnormal capillary proliferation in hemophiliac joints, and a disorder of the female reproductive system or metastasis of cancer cells.

17. The method of claim 7 wherein the condition is selected from the group consisting of restenosis, arthritis, psoriasis, diabetic retinopathy, retinopathy of prematurity, macular degeneration, scleroderma, hemangioma, retrolental fibroplasia, abnormal capillary proliferation in hemophiliac joints, and a disorder of the female reproductive system or metastasis of cancer cells.

18. The method of claim 12 wherein the condition is selected from the group consisting of restenosis, arthritis, psoriasis, diabetic retinopathy, retinopathy of prematurity, macular degeneration, scleroderma, hemangioma, retrolental fibroplasia, abnormal capillary proliferation in hemophiliac joints, and a disorder of the female reproductive system or metastasis of cancer cells.

19. The method of claim 1 wherein the compound is tamoxifen benzyl bromide.

* * * * *

UNITED STATES PATENT AND TRADEMARK OFFICE
CERTIFICATE OF CORRECTION

PATENT NO. : 6,387,955 B1
DATED : May 14, 2002
INVENTOR(S) : Biegon et al.

It is certified that error appears in the above-identified patent and that said Letters Patent is hereby corrected as shown below:

<u>Title page,</u>
Item [73], Assignee, change "Rehovot (IL)" to -- New York, NY --.
Item [57], ABSTRACT,
Formulas I and II, change "$R^5$" to -- $R_5$ --.
Item [56], References Cited, OTHER PUBLICATIONS, delete the second occurrence of "vol. 129,".

Signed and Sealed this

Seventeenth Day of December, 2002

JAMES E. ROGAN
*Director of the United States Patent and Trademark Office*